United States Patent
Siegner et al.

(10) Patent No.: US 8,236,859 B2
(45) Date of Patent: Aug. 7, 2012

(54) USE OF 3-(4-HYDROXY- 3-METHOXYPHE-NYL)-1- (4-HYDROXYPHENYL) PROPA-NE-1-ONE FOR IMPROVED SKIN CONTOURING OR AGAINST CELLULITE

(75) Inventors: Ralf Siegner, Pinneberg (DE); Ursula Holtzmann, Hamburg (DE); Julia Eckert, Hamburg (DE); Stefan Heuser, Hamburg (DE); Marc Winnefeld, Hamburg (DE)

(73) Assignee: Beiersdorf AG, Hamburg (DE)

( * ) Notice: Subject to any disclaimer, the term of this patent is extended or adjusted under 35 U.S.C. 154(b) by 330 days.

(21) Appl. No.: 12/354,285

(22) Filed: Jan. 15, 2009

(65) Prior Publication Data
US 2009/0209651 A1    Aug. 20, 2009

(30) Foreign Application Priority Data
Feb. 18, 2008   (DE) .......................... 10 2008 009 758

(51) Int. Cl.
*A61K 31/12* (2006.01)
(52) U.S. Cl. ....................................... 514/685
(58) Field of Classification Search .......................... None
See application file for complete search history.

(56) References Cited

U.S. PATENT DOCUMENTS

| 5,496,565 A | 3/1996 | Heinze et al. |
| 2008/0242740 A1 | 10/2008 | Ley et al. |
| 2010/0204343 A1* | 8/2010 | Koch et al. .................... 514/772 |

FOREIGN PATENT DOCUMENTS

| DE | 43 08 282 A1 | 9/1994 |
| EP | 1 818 060 | 8/2007 |
| EP | 1 977 655 | 10/2008 |
| FR | 2 578 165 | 9/1986 |
| WO | 2007/107596 A1 | 9/2007 |
| WO | 2007/122421 A2 | 11/2007 |

OTHER PUBLICATIONS

Khan et al., Journal of the American Academy of Dermatology, (2010), 62(3), pp. 373-384.*
English language Abstract of FR 2 578 165, (1986).

* cited by examiner

*Primary Examiner* — Phyllis G. Spivack
(74) *Attorney, Agent, or Firm* — Abel Law Group, LLP

(57) ABSTRACT

A cosmetic or dermatological preparation which is suitable for application to skin and comprises 3-(4-hydroxy-3-methoxyphenyl)-1-(4-hydroxyphenyl)-propane-1-one in a concentration which is effective for at least one of increasing skin moisture content, moisturizing skin, improving the surface structure of the skin, reducing cellulite, increasing the resilience and elasticity of skin, strengthening the connective tissue of skin, and reducing stretch marks on skin. This Abstract is not intended to define the invention disclosed in the specification, nor intended to limit the scope of the invention in any way.

20 Claims, No Drawings

USE OF 3-(4-HYDROXY-3-METHOXYPHE-NYL)-1-(4-HYDROXYPHENYL) PROPA-NE-1-ONE FOR IMPROVED SKIN CONTOURING OR AGAINST CELLULITE

CROSS-REFERENCE TO RELATED APPLICATIONS

The present application claims priority under 35 U.S.C. §119 of German Patent Application No. 10 2008 009 758.6, filed Feb. 18, 2008, the entire disclosure of which is expressly incorporated by reference herein.

BACKGROUND OF THE INVENTION

1. Field of the Invention

The present invention relates to the cosmetic or dermatological use of 3-(4-hydroxy-3-methoxyphenyl)-1-(4-hydroxyphenyl)-propane-1-one for improved skin contouring or against cellulite, respectively.

2. Discussion of Background Information

Cosmetics can cover all measures that are used for esthetic reasons to change the skin and hair or that are used to clean the body. Cosmetics therefore means to care for, to improve and to beautify the body's appearance, in order to please others as well as oneself in a manner that can be seen, felt and smelt.

The aim of skin care is furthermore to compensate for the loss by the skin of grease and water caused by daily washing. This is particularly important when the natural regenerative capacity is not sufficient. Furthermore, skin care products should protect against environmental influences, in particular against sun and wind, and delay skin aging.

Chronological skin aging is caused, e.g., by endogenic, genetically determined factors. The following structural damage and functional disorders, also covered by the term "senile xerosis," for example, occur in the epidermis and the dermis as a result of aging:
a) Dryness, roughness and formation of dryness wrinkles,
b) Itching and
c) Reduced regreasing by sebaceous glands (e.g., after washing).

Exogenous factors, such as UV light and chemical noxae, can have a cumulative effect and, for example, accelerate or supplement the endogenous aging processes. In the epidermis and dermis, for example, the following structural damage and functional disorders arise in the skin in particular as a result of exogenous factors; these are more far-reaching than the degree and quality of the damage in the case of chronological aging:
d) Visible vascular dilation (teleangiectases, cuperosis);
e) Flaccidity and formation of wrinkles;
f) Local hyperpigmentation, hypopigmentation and abnormal pigmentation (e.g., senile keratoses) and
g) Increased susceptibility to mechanical stress (e.g., cracking).

The present invention relates in particular to products for the care of skin that has aged naturally and to the phenomena listed under a), e) and g).

Products for the care of flaccid, in particular aged skin are known per se. They comprise, for example, retinoids (vitamin A acid and/or derivatives thereof) or vitamin A and/or derivatives thereof. Their effect on structural damage is, however, limited in terms of scope. Furthermore, in product development, there are considerable difficulties in stabilizing the active ingredients to an adequate extent against oxidative decay. The use of products containing vitamin A acid, moreover, often causes severe erythematous skin irritations. Retinoids can therefore only be used in low concentrations.

Flaccid skin is often also associated with an accompanying phenomenon of excess weight and/or so-called cellulite, which is often associated therewith.

The body awareness of consumers has increased significantly in recent years. In this connection, as well as cleansing and care applications, measures are increasingly being taken to improve the silhouette of the body. Cellulite—a widespread phenomenon—assumes a central position in this respect. The visible appearance of cellulite is based on an increase of fatty bodies in the subcutis (subcutaneous fatty tissue), a weakening of the connective tissue and a reduction in the through-flow ratio in the blood stream and lymphatic tract. The cause is therefore a partly constitutional weakening of the connective tissue with the simultaneous occurrence of enlarged fatty cell chambers as a result of excess weight, an unbalanced diet and lack of exercise. The formation of cellulite can also be attributed to increased permeability of the capillary walls, which permits penetration of water into the connective tissue.

In addition, there may be a localized testosterone deficiency in the areas of the affected skin. In any case, cellulite is a phenomenon which is almost never observed in men.

Stretch marks (striae) are the visible phenomena in the subcutis, which can occur through pronounced stretching of the skin, for example, during pregnancy (striae gravidarum) or in the case of rapid weight gain or with excess weight. The coloring is caused by the blood vessels shining through. The stretch marks preferably occur on tissue under particular strain such as stomach, hips, buttocks, upper arms and breasts.

It would be desirable therefore, to find ways to avoid the disadvantages of the prior art. In particular, it would be desirable to provide preparations which can effect an advantageous tightening of flaccid skin.

It would also be advantageous to be able to provide skin care preparations which are designed to care for and beautify the appearance. The preparations should in particular improve the moisture content of the skin.

SUMMARY OF THE INVENTION

The present invention provides method of at least one of increasing the moisture content of the skin, moisturizing skin, improving the surface structure of skin, reducing cellulite, increasing the resilience and elasticity of skin, strengthening the connective tissue of skin, and reducing stretch marks on skin, wherein in the method comprises applying to the skin an effective amount of a preparation which comprises 3-(4-hydroxy-3-methoxyphenyl)-1-(4-hydroxyphenyl)-propane-1-one.

In one aspect of the method, the preparation may be a cosmetic or dermatological preparation which comprises from about 0.0001% to about 30% by weight, for example, from about 0.001% to about 10% by weight, from about 0.01% to about 10% by weight, from about 0.05% to about 5% by weight, or from about 0.1% to about 2% by weight of 3-(4-hydroxy-3-methoxyphenyl)-1-(4-hydroxyphenyl)-propane-1-one.

The present invention also provides a cosmetic or dermatological preparation which is suitable for application to skin and comprises 3-(4-hydroxy-3-methoxyphenyl)-1-(4-hydroxyphenyl)-propane-1-one in a concentration which is effective for one or more of increasing the moisture content of the (human) skin, moisturizing skin, improving the surface structure of the skin, reducing cellulite, increasing the resilience and elasticity of the skin, strengthening the connective tissue of the skin, and reducing stretch marks on the skin.

In one aspect, the preparation may comprise from about 0.01% to about 10% by weight, e.g., from about 0.05% to about 5% by weight, or from about 0.1% to about 2% by weight of 3-(4-hydroxy-3-methoxyphenyl)-1-(4-hydroxyphenyl)-propane-1-one.

In another aspect, the preparation may be present as a lotion, a cream, a gel, or a serum.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

Surprisingly, it has been found that a cosmetic preparation which comprises a cosmetically effective quantity of 3-(4-hydroxy-3-methoxyphenyl)-1-(4-hydroxyphenyl)-propane-1-one overcomes the disadvantages of the prior art.

The use of preparations according to the present invention with a cosmetically effective quantity of 3-(4-hydroxy-3-methoxyphenyl)-1-(4-hydroxyphenyl)-propane-1-one, for example, in the form of the cited examples, surprisingly leads to a considerable improvement in the appearance of the skin. In particular, through the application of preparations according to the invention the barrier properties of the skin can be maintained or restored,
the drying out of the skin can be better counteracted and
the skin can be better protected against environmental influences.

Further, through the use of preparations according to the present invention, the skin moisture and the deep moisture of the skin can be improved. This skin care effect and the protection from loss of moisture may last for several hours or even for the entire day or even longer.

The use of cosmetic preparations which comprise a cosmetically effective quantity of 3-(4-hydroxy-3-methoxyphenyl)-1-(4-hydroxyphenyl)-propane-1-one, for increasing the skin moisture or for moisturizing the skin is therefore in accordance with the invention.

It was furthermore surprising that the elasticity of the skin, the hair and/or the nails and therefore cellulite or the phenomenon of the so-called "orange-peel skin" can be improved through the application of preparations according to the present invention.

The use of 3-(4-hydroxy-3-methoxyphenyl)-1-(4-hydroxyphenyl)-propane-1-one for increasing the resilience and elasticity of the skin is also in accordance with the present invention.

The use of 3-(4-hydroxy-3-methoxyphenyl)-1-(4-hydroxyphenyl)-propane-1-one for strengthening the connective tissue of the skin is in accordance with the present invention as well.

The use of 3-(4-hydroxy-3-methoxyphenyl)-1-(4-hydroxyphenyl)-propane-1-one for reducing stretch marks on the skin is also in accordance with the present invention.

Cosmetic or dermatological preparations according to the present invention preferably contain from about 0.001% to about 30% by weight, preferably from about 0.1% to 15% by weight, particularly preferably from about 0.5% to 5% by weight of 3-(4-hydroxy-3-methoxyphenyl)-1-(4-hydroxyphenyl)-propane-1-one, based on the total weight of the preparation.

Preparation methods for 3-(4-hydroxy-3-methoxyphenyl)-1-(4-hydroxyphenyl)-propane-1-one of formula:

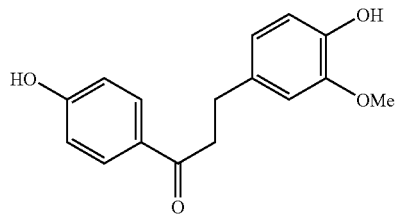

advantageously consist of or comprise the following steps:
a) conversion of p-hydroxyacetophenone with vanillin to 3-(4-hydroxy-3-methoxyphenyl)-1-(4-hydroxyphenyl)-2-propene-1-one and
b) hydrogenation of the 3-(4-hydroxy-3-methoxyphenyl)-1-(4-hydroxyphenyl)-2-propene-1-one obtained in step a) to form 3-(4-hydroxy-3-methoxyphenyl)-1-(4-hydroxyphenyl)-propane-1-one.

In a preferred embodiment of the preparation method for the compound of formula 1 of the present invention, the conversion of p-hydroxyacetophenone with vanillin in step a) is carried out such that p-hydroxyacetophenone and vanillin are added to a mixture of potassium hydroxide in diethylene glycol dimethyl ether at elevated temperature. The temperature is usually in the range of from about 50° C. to about 200° C., preferably in the range of from about 80° C. to about 140° C., further preferably in the range of from about 100° C. to about 120° C.

Subsequently the resultant compound is hydrolyzed to 3-(4-hydroxy-3-methoxyphenyl)-1-(4-hydroxyphenyl)-2-propene-1-one. The pH value is preferably adjusted in the range of from about 6 to about 7.

In a preferred embodiment of the preparation method according to the present invention for the compound of formula 1, the hydrogenation of the 3-(4-hydroxy-3-methoxyphenyl)-1-(4-hydroxyphenyl)-2-propene-1-one to form 3-(4-hydroxy-3-methoxyphenyl)-1-(4-hydroxyphenyl)-propane-1-one is carried out such that the 3-(4-hydroxy-3-methoxyphenyl)-1-(4-hydroxyphenyl)-2-propene-1-one produced is dissolved in tetrahydrofuran and a suitable quantity of Pd on activated carbon catalyst (for example, Pd content: about 5% by weight, water content about 50% by weight, based on the total mass of the catalyst) is added thereto. Preferably the reaction is carried out at normal pressure and further preferably at room temperature (about 20° C.).

Synthesis Example for 3-(4-hydroxy-3-methoxyphenyl)-1-(4-hydroxyphenyl)-1-propanone (a) Conversion of p-hydroxyacetophenone with vanillin:
Potassium hydroxide (20 g) in 100 g of diethylene glycol diethyl ether is heated to 120° C. while being stirred, and added to a mixture of 14 g of p-hydroxyacetophenone and 15 g of vanillin within 1 h. Upon completion of the addition stirring is continued for another 20 min., a hydrolysis is carried out and the pH is adjusted to 6-7. After phase separation, the solvent is removed and 25 g of 3-(4-hydroxy-3- methoxyphenyl)-1-(4-hydroxyphenyl)-2-propene-1-one is obtained. Yield: 93% of the theory.

(b) Hydrogenation of the reaction product obtained in step (a):

3-(4-Hydroxy-3-methoxyphenyl)-1-(4-hydroxyphenyl)-2-propene-1-one (10 g) is dissolved in 100 g tetrahydrofuran, 0.2 g of Pd on activated carbon (Pd content: about 5% by weight, water content approx. 50% by weight, based on the total mass of the catalyst) is added and a hydrogenation is carried out at normal pressure and room temperature (approx. 20° C.). After removal of the catalyst and the solvent, 9 g of 3-(4-hydroxy-3-methoxyphenyl)-1-(4-hydroxyphenyl)-propane-1-one is obtained. Yield: 89% of the theory.

Spectroscopic data of 3-(4-hydroxy-3-methoxyphenyl)-1-(4-hydroxyphenyl)-propane-1-one (formula 1):

$^{13}$C-NMR (CDCl$_3$; 75.5 MHz): δ (ppm)=197.42 (s), 161.85 (s), 147.24 (s), 144.44 (s), 132.03 (s), 130.37 (d), 130.37 (d), 128.18 (s), 120.27 (d), 115.11 (d), 115.07 (d), 115.07 (d), 112.53 (d), 55.42 (q), 39.30 (t), 29.42 (t);

MS: m/z (%)=M$^+$-ion 272 (82), 151 (24), 137 (77), 121 (100), 93 (19), 65 (22).

The cosmetic or dermatological preparations according to the present invention can have a conventional composition and can be used for the treatment, the care and the cleansing of the skin and/or the hair and as a cosmetic product in decorative cosmetics.

They preferably contain from about 0.001% to about 10% by weight, preferably from about 0.05% to about 5% by weight, in particular from about 0.1% to about 2.0% by weight, based on the total weight of the preparation, of 3-(4-hydroxy-3-methoxyphenyl)-1-(4-hydroxyphenyl)-propane-1-one.

Cosmetic and dermatological preparations according to the present invention can be present in different forms. Thus, for example, they can be present as a solution, an anhydrous preparation, an emulsion or a microemulsion of the water-in-oil (W/O) type, or oil-in-water (O/W) type, a multiple emulsion, for example, of the water-in-oil-in-water (W/O/W) type, a gel, a solid stick, an ointment or an aerosol.

According to the present invention it may also be advantageous to apply 3-(4-hydroxy-3-methoxyphenyl)-1-(4-hydroxyphenyl)-propane-1-one in encapsulated form, e.g., in collagen matrices and other conventional encapsulation materials, e.g., as cellulose encapsulations, in gelatin, wax matrices or liposomally encapsulated. In particular wax matrices as described in DE OS 43 08 282, the entire disclosure whereof is incorporated by reference herein, can have proven to be favorable.

It is also possible and advantageous for the purposes of the present invention to incorporate 3-(4-hydroxy-3-methoxyphenyl)-1-(4-hydroxyphenyl)-propane-1-one into aqueous systems or surfactant preparations for cleansing the skin and the hair.

The cosmetic and dermatological preparations according to the present invention can comprise cosmetic auxiliary agents, such as those which are conventionally used in such preparations, e.g., preservatives, bactericides, perfumes, antifoaming agents, dyes, pigments with a coloring effect, thickeners, surfactants, emulsifiers, softening, moistening and/or moisture-retaining substances, fats, oils, waxes or other usual components of a cosmetic or dermatological formulation such as alcohols, polyols, polymers, gelling agents, foam stabilizers, electrolytes, organic solvents or silicone derivatives.

Advantageous gelling agents for preparations of this type include, for example, copolymers of C$_{10-30}$ alkyl acrylates and one or more monomers of acrylic acid, methacrylic acid, or esters thereof. The INCI designation for compounds of this type is "acrylates/C10-30 alkyl acrylate crosspolymer." Especially advantageous are the Pemulen® grades TR1, TR2 and TRZ from Goodrich (Noveon).

Carbopols are also advantageous gelling agents for preparations of this type. Carbopols are polymers of acrylic acid, in particular also acrylate-alkyl acrylate copolymers. Advantageous carbopols are, for example, the grades 980, 981, 984, 1342, 1382, 2984 and 5984, likewise the ETD grades 2001, 2020, 2050 and Carbopol Ultrez 10, PVM/MA decadiene crosspolymer (trade name Stabileze® 06), polyglyceryl methacrylate, and polyacrylamide, ammonium dimethyl tauramide/vinylformamide copolymers, copolymers or crosspolymers comprising acryloyldimethyltaurate, polyacryloyldimethyltauramide, polyvinylpyrrolidone and copolymers thereof.

Further examples of advantageous gelling agents for such preparations include xanthan gum, polyvinylpyrrolidone, cellulose derivatives, in particular cellulose ethers, such as, for example, hydroxypropyl methylcellulose, starch and starch derivatives, hyaluronic acid, carrageenan, silicon dioxide and aluminum silicates.

The concentration of (optional) antioxidants (one or more compounds) in the preparations of the present invention is preferably from about 0.001% to about 30% by weight, particularly preferably from about 0.05% to about 20% by weight, in particular from about 1% to about 10% by weight, based on the total weight of the preparation.

The lipid phase may advantageously be chosen from the following substances:

Mineral oils, mineral waxes

Oils, such as triglycerides of capric acid or caprylic acid, and also natural oils, such as, for example, castor oil, Fats, waxes and other natural and synthetic fatty bodies, preferably esters of fatty acids with alcohols of low C number, e.g. with isopropanol, propylene glycol or glycerol, or esters of fatty alcohols with alkanoic acids of low C number or with fatty acids;

Alkyl benzoates;

Silicone oils, such as dimethicones, cyclomethicones, dimethylpolysiloxanes, diethylpolysiloxanes, diphenylpolysiloxanes, and mixed forms thereof.

The oil phase of the emulsions, oleogels, hydrodispersions or lipodispersions for the purposes of the present invention may advantageously be selected from esters of saturated and/or unsaturated, branched and/or unbranched alkanecarboxylic acids with a chain length of from about 3 to about 30 C atoms, and saturated and/or unsaturated, branched or unbranched alcohols with a chain length of from about 3 to about 30 C atoms, and from esters of aromatic carboxylic acids and saturated and/or unsaturated, branched and/or unbranched alcohols with a chain length of from about 3 to about 30 C atoms. Such ester oils can, for example, advantageously be selected from isopropyl myristate, isopropyl palmitate, isopropyl stearate, isopropyl oleate, n-butyl stearate, n-hexyl laureate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, as well as synthetic, semisynthetic, and natural mixtures of such esters, for example, jojoba oil.

Optionally, the aqueous phase of the preparations of the present invention may advantageously comprise alcohols, diols, or polyols having a low number of C atoms, as well ethers thereof, preferably ethanol, isopropanol, propylene glycol, glycerin, ethylene glycol, ethylene glycol monoethyl or monobutyl ether, propylene glycol monomethyl, monoethyl, or monobutyl ether, diethylene glycol monomethyl or monoethyl ether, and analogous products, furthermore alcohols having a low number of C atoms, for example, ethanol, isopropanol, 1,2-propanediol, glycerin, as well as in particular one or more thickeners, which can advantageously be selected from silicon dioxide, aluminum silicate, polysaccharides or derivatives thereof, e.g., hyaluronic acid, xanthan gum hydroxypropylmethylcellulose, particularly preferably from polyacrylates, preferably a polyacrylate from the so-called carbopols, for example, carbopols of the types 980, 981, 1382, 2984, 5984 respectively, individually or in combination.

In particular mixtures of the above-referenced solvents may be used. With alcoholic solvents, water may be a further constituent.

Emulsions according to the present invention are advantageous and may contain, e.g., the referenced fats, oils, waxes and other fatty bodies, as well as water and an emulsifier, such as is conventionally used for this type of formulation.

Gels according to the present invention will usually contain alcohols of low C number, e.g. ethanol, isopropanol, 1,2-propanediol, glycerol and water, or one or more of the oils cited above in the presence of a thickener, which in the case of oily/alcoholic gels preferably is silicon dioxide or an aluminum silicate, and in the case of aqueous/alcoholic or alcoholic gels preferably is a polyacrylate.

As a propellant for preparations according to the invention that can be sprayed from aerosol containers, the highly volatile, liquefied propellants, for example, hydrocarbons (propane, butane, isobutane) are suitable, which can be used alone or in combination with one another. Compressed air can also be used advantageously.

Advantageously, preparations according to the invention may also contain one or more substances which absorb UV radiation in the UVA and/or UVB range, with the total amount of the filter substances being, for example, from about 0.1% to about 30% by weight, preferably from about 0.5% to about 10% by weight, in particular, from about 1% to about 6% by weight, based on the total weight of the preparations, in order to provide cosmetic preparations that protect the hair or the skin from ultraviolet radiation. They can also be used as sunscreen for the hair or the skin.

The following examples illustrate the present invention without limiting the scope thereof. Unless stated otherwise, all amounts, proportions and percentages are percentages by weight, based on the weight of the total quantity or on the total weight of the preparations.

| Firming lotion with 3-(4-hydroxy-3-methoxyphenyl)-1-(4-hydroxyphenyl)-1-propanone | % by weight |
|---|---|
| Paraffinum Liquidum | 10 |
| Glyceryl stearate SE | 1.5 |
| Stearic acid | 1 |
| Glycerol | 10 |
| Carbomer | 0.2 |
| Xanthan gum | 1 |
| Caffeine | 0.5 |
| Alcohol denat. | 3 |
| Coenzyme Q 10 | 0.03 |
| Dimethicone | 2 |
| Cyclomethicone | 3 |
| 3-(4-hydroxy-3-methoxyphenyl)-1-(4-hydroxyphenyl)-1-propanone | 0.1 |
| Perfume | 0.2 |
| Preservative | q.s. |
| Water | ad 100 |

| Anti-cellulite cream | % by weight |
|---|---|
| PEG-40 stearate | 1.8 |
| Cetyl alcohol | 3 |
| Glyceryl stearate | 3 |
| Dimethicone | 2 |
| Paraffinum liquidum | 3 |
| Glycerol | 8 |
| Carbomer | 0.2 |
| Caprylic acid/capric acid triglycerides | 3 |
| 3-(4-hydroxy-3-methoxyphenyl)-1-(4-hydroxyphenyl)-1-propanone | 0.5 |
| EDTA | 0.2 |
| Caffeine | 2 |
| Preservative | q.s. |
| Water | ad 100 |

| Anti-cellulite gel | % by weight |
|---|---|
| Sodium polyacrylate | 0.4 |
| Chondrus Chrispus | 0.1 |
| Carbomer | 0.3 |
| Cyclomethicone | 4 |
| Glycerol | 8 |
| Dimethiconol | 2 |
| Alcohol denat. | 10 |
| Ginkgo biloba | 0.1 |
| Aescin | 0.05 |
| Carnitine | 0.3 |
| Caffeine | 0.2 |
| 3-(4-hydroxy-3-methoxyphenyl)-1-(4-hydroxyphenyl)-1-propanone | 0.2 |
| Water | ad 100 |

| Anti-cellulite serum | % by weight |
|---|---|
| Acrylates/C 10-30 alkyl acrylate crosspolymer | 0.5 |
| Xanthan gum | 0.2 |
| Cetearyl alcohol | 1 |
| Dimethicone | 1 |
| Cyclomethicone | 5 |
| Glycerol | 4 |
| Hydrogenated polyisobutene | 2 |
| Alcohol denat. | 10 |
| Phenoxyethanol | 0.4 |
| Methyl paraben | 0.2 |
| 3-(4-hydroxy-3-methoxyphenyl)-1-(4-hydroxyphenyl)-1-propanone | 0.5 |
| Water | ad 100 |

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method of improving a condition of skin, wherein in the method comprises applying to skin in need thereof a preparation which comprises 3-(4-hydroxy-3-methoxyphenyl)-1-(4-hydroxyphenyl)-propane-1-one in an amount which is effective for at least one of increasing the moisture content of skin, moisturizing skin, improving the surface structure of skin, reducing cellulite, increasing the resilience and elasticity of skin, strengthening the connective tissue of skin, and reducing stretch marks on skin, the preparation further comprising at least one of caffeine, carnitine, and coenzyme Q10.

2. The method of claim 1, wherein the moisture content of the skin is increased.

3. The method of claim 1, wherein the skin is moisturized.

4. The method of claim 1, wherein the surface structure of skin is improved.

5. The method of claim 4, wherein the method comprises a smoothing of the skin.

6. The method of claim 4, wherein the method comprises a reduction of skin dimples.

7. The method of claim 1, wherein cellulite is reduced.

8. The method of claim 1, wherein the resilience and elasticity of the skin is increased.

9. The method of claim 1, wherein the connective tissue of the skin is strengthened.

10. The method of claim 1, wherein stretch marks on the skin are reduced.

11. The method of claim 1, wherein the preparation comprises from about 0.1% to about 2% by weight of 3-(4-hydroxy-3-methoxyphenyl)-1-(4-hydroxyphenyl)-propane-1-one.

12. A cosmetic or dermatological preparation, wherein the preparation is suitable for application to skin and comprises 3-(4-hydroxy-3-methoxyphenyl)-1-(4-hydroxyphenyl)-propane-1-one and at least one of caffeine, carnitine, and coenzyme Q10.

13. The preparation of claim 12, wherein the preparation comprises from about 0.1% to about 2% by weight of 3-(4-hydroxy-3-methoxyphenyl)-1-(4-hydroxyphenyl)-propane-1-one.

14. The preparation of claim 12, wherein the preparation is present as a lotion, a cream, a gel, or a serum.

15. The preparation of claim 12, wherein the preparation comprises caffeine.

16. The preparation of claim 12, wherein the preparation comprises carnitine.

17. The preparation of claim 12, wherein the preparation comprises coenzyme Q10.

18. The preparation of claim 12, wherein the preparation comprises from about 0.001% to about 10% by weight of 3-(4-hydroxy-3-methoxyphenyl)-1-(4-hydroxyphenyl)-propane-1-one.

19. The preparation of claim 12, wherein the preparation comprises from about 0.01% to about 10% by weight of 3-(4-hydroxy-3-methoxyphenyl)-1-(4-hydroxyphenyl)-propane-1-one.

20. The preparation of claim 12, wherein the preparation comprises from about 0.05% to about 5% by weight of 3-(4-hydroxy-3-methoxyphenyl)-1-(4-hydroxyphenyl)-propane-1-one.

* * * * *